United States Patent [19]

Birks et al.

[11] Patent Number: 4,847,207
[45] Date of Patent: Jul. 11, 1989

[54] PROCESS FOR DETECTION OF ORGANOSULFUR COMPOUNDS AND APPARATUS THEREFOR

[75] Inventors: John W. Birks; Julie N. Getty; Richard H. Getty, all of Boulder, Colo.

[73] Assignee: University Patents, Inc., Westport, Conn.

[21] Appl. No.: 157,188

[22] Filed: Feb. 16, 1988

Related U.S. Application Data

[63] Continuation of Ser. No. 901,109, Aug. 28, 1986, abandoned, which is a continuation of Ser. No. 645,444, Aug. 29, 1984, abandoned.

[51] Int. Cl.$^4$ .................. G01N 21/49; G01N 21/76
[52] U.S. Cl. ..................................... 436/120; 436/104; 436/161; 436/172; 422/52
[58] Field of Search ............... 422/52; 436/120, 161, 436/104, 172

[56] References Cited

U.S. PATENT DOCUMENTS

| | | | |
|---|---|---|---|
| 3,528,779 | 9/1970 | Fontijn | 422/52 X |
| 4,018,562 | 4/1977 | Parks et al. | 422/52 X |
| 4,049,383 | 9/1977 | Burton et al. | 422/52 X |
| 4,301,114 | 11/1981 | Rounbehler et al. | 422/52 |

OTHER PUBLICATIONS

Duewer et al, J. Chem. Phys., 58(6), pp. 2310–2320, Mar. 15, 1973.
Nelson et al, Anal Chem, 55(11), Sep. 1983.
Nelson, Thesis, Univ. of Colorado, 1984.
D. J. Bogan, D. W. Setser, J. P. Sung, J. Phys. Chem, 18, No. 9, 1977, pp. 888–905.
D. J. Bogan, D. W. Setser, J. Chem. Phys., vol. 64, No. 2, 1976, pp. 586–602.
K. C. Kim, D. W. Setser, J. Phys. Chem, vol. 77, No. 21, 1973, pp. 2493–2498.

Primary Examiner—Barry S. Richman
Assistant Examiner—Lynn M. Kummert
Attorney, Agent, or Firm—Barbara A. Shimei

[57] ABSTRACT

An organosulfur compound is detected and/or quantified, optionally in admixture with one or more other compounds, by reacting the organosulfur compound with gaseous fluorine at sub-atmospheric pressure and observing the chemiluminescence which develops. Detections at ultra-trace levels are achieved. A special detector cell is provided in which the reaction is performed.

17 Claims, 4 Drawing Sheets

PROCESS FOR DETECTION OF ORGANOSULFUR COMPOUNDS AND APPARATUS THEREFOR

This is a continuation of application Ser. No. 901,109 filed 8/28/86, now abandoned, which in turn is a continuation of application Ser. No. 645,444, filed 8/29/84, now abandoned.

The present invention relates to a process for the detection of certain sulfur-containing compounds and to an apparatus useful in the employment of said process. More particularly the invention relates to a process for detecting certain organic compounds containing a least one sulfur atom and at least one fluorine-reactive hydrogen atom (hereinafter referred to as "organosulfur compounds") by reacting said organosulfur compounds with elemental fluorine and observing the resulting chemiluminescence.

This invention resulted in part from work supported by a National Science Foundation grant. Further information concerning this grant, the work and the present invention appears in the article "Fluorine Induced Chemiluminescence Detector for Reduced Sulfur Compounds," *Anal. Chem.* 1983, 55, 176, and in the doctoral thesis of Julie Nelson Getty which has been submitted to the University of Colorado. A copy of said article and of said thesis are attached and are hereby incorporated by reference into the present specification.

In recent years it has become important to detect organosulfur compounds in trace and even ultra-trace amounts, that is, in amounts of one part per million or billion. Analytical methods of this sensitivity are desired for such purposes as, for example, the detection of residual pesticides and fungicides on vegetables and fruits; for the detection toxic chemicals including drugs in animals and athletes; for the detection of toxic vapors in the air of factories and laboratories; and for the detection of contaminants in water. A process which is capable of detecting such compounds rapidly and in simple and compact apparatus is particularly desired.

The invention is a process for detecting an organosulfur compound containing at least one fluorine-reacting hydrogen atom and at least one sulfur atom, which process comprises reacting in gaseous medium an effective amount of molecular fluorine with said organosulfur compound to form vibrationally excited hydrogen fluoride therefrom, and detecting the chemiluminescence which is produced when said excited hydrogen fluoride decays to its ground state. The reason why the process of the present invention detects only organosulfur compounds, that is, only compounds which contain carbon and sulfur atoms, is not known, and applicants do not wish to be bound by any theory.

The invention further is a process for detecting an organosulfur compound in admixture with at least one other compound not having this composition, which comprises passing said admixture into a chromatographic column thereby retaining the components of said admixture as fractions on separatant in said column, eluting said fractions from said separatant, passing said fractions into a reaction vessel containing fluorine, thereby forming vibrationally excited hydrogen fluoride by reaction of said organosulfur compound with said fluorine under reduced pressure, and detecting the chemiluminescence which is produced when said hydrogen fluoride decays to its ground state. Formation of this hydrogen fluoride and the decay thereof take place very rapidly.

The apparatus preferred for performing the reaction comprises in combination a substantially chemically inert cylinder having a closed bottom and an open flanged top; a first sleeved port at a mid level of said cylinder adapted to receive a tube for admission of said organosulfur compound into said cylinder; a second sleeved port at a mid level of said cylinder adapted to receive a tube for admission of gaseous fluorine into said cylinder; a third sleeved port adapted to receive a tube for withdrawal of gas from said cylinder; and a transparent window which is sealed vacuum-tight to said flange, thereby closing the top of said cylinder.

The invention results from our discovery that when organic compounds which contain at least one fluorine-reactive hydrogen atom and at least one sulfur atom are reacted with fluorine in gaseous state at reduced pressure, hydrogen fluoride in highly vibrationally excited state is formed very rapidly in high yields; that this hydrogen fluoride spontaneously decays very rapidly to its ground state with emission of chemiluminescence in the characterizing 650–750 nm red band; that the luminescence possesses a sharp characterizing peak in the 700–715 nm wavelength band; that formation of such highly excited hydrogen fluoride, which releases the spectrum of red light on decay, is unique to compounds of the group mentioned; and that therefore the aforementioned process permits selective detection of these compounds even in the presence of compounds of different composition. In other words, while many organic compounds react with fluorine to yield vibrationally excited hydrogen fluoride, chemiluminescence having wavelengths in the 650–750 nm range with peaking in the 700–715 nm waveband occurs only in the decay of highly vibrationally excited hydrogen fluoride derived from organosulfur compounds under the conditions mentioned. The process of the present invention thus achieves selective detection of these compounds.

The invention possesses the following principal advantages.

1. The process is linearly responsive to the concentration of analyte (the compound to be detected) in the test samples. The intensity of the chemiluminescence which is produced in the broad 650–750 nm band and particularly in the 700–715 nm band is a linear function of the amount of organosulfur compound present in the sample. The process therefore permits quantitative analysis to be made by direct comparison between the chemiluminescence of the analyte or analytes in the test sample and the reference sample or samples.

2. The intensity of the chemiluminescence which is produced in the aforementioned bands is not affected by the presence or absence of even large amounts of hydrocarbons in the the test sample. The process is thus not subject to hydrocarbon quenching. Furthermore, the process is not affected by the presence of certain compounds often found in industrial gases. There is thus no interference from the following gases: water vapor, $H_2S$, gaseous sulfur, $CO$, $CO_2$, $SO_2$, $SO_3$, $NH_3$, $HCl$, $CCl_4$, $CF_2Cl_2$, $SCl_2O_2$, $CH_4$, $C_6H_6$, $N_2$ and $O_2$.

The reaction or reactions which lead to the formation of the very highly excited hydrogen fluoride referred to above and the decay of this compound to ground state are not known, and applicants do not wish to be bound by any theory.

The process of the present invention can be performed by passing the organosulfur compound to be detected into a reaction vessel containing elemental fluorine (or sulfur hexafluoride or carbon tetrafluoride which release fluorine), viewing the interior of the vessel through a light filter which is opaque to light outside the 650–750 nm wavelength band, and detecting the chemiluminescence which develops during the decay of the vibrationally excited hydrogen fluoride to ground state, thereby detecting the presence of the organosulfur compound. This chemiluminescence is sufficiently bright to be detectable by the naked eye in the dark. However, it is preferred to detect the chemiluminescence by a photomultiplier tube.

To ensure maximum intensity of the chemiluminescence it is advantageous for the fluorine or compound providing fluorine to be present in excess, and a great excess does no harm and may be an advantage. Hence it is preferred to introduce the fluorine into the detector cell in a ratio between about 100 and 1,000 times or more of the estimated weight of the organosulfur compound. The organosulfur compound to be detected is normally present in its carrier gas in only trace amount, that is, between about $10^{-3}$ and $10^{-8}$ or less of the weight of the carrier gas.

The invention is broadly applicable to all organosulfur compounds, including thiols, sulfides and thioesters.

Organosulfur compounds which are difficult to volatilize can be reacted in the form of colloidal aerosol particles, produced by passing a solution of the organosulfur compound in a volatile solvent into the reaction vessel having a temperature above the temperature at which the solvent volatilizes but below the volatilization temperature of the solute. Alternatively the aerosol can be formed by passing the solution into a volatilizer immediately outside of the reaction vessel.

When the sample to be analyzed contains two or more organosulfur compounds and if it is desired to quantify them, the sample is advantageously passed through a chromatographic column containing an appropriate adsorbent or partitioning liquid (herein termed "separatant") whereon the organosulfur compounds are separated from each other and the resulting fractions are eluted consecutively from the column. Each organosulfur eluent is reacted with fluorine according to the process of the present invention. Preferably, the intensity of the luminescence is recorded as it waxes and wanes on a strip recording chart as a function of time, thereby showing the interval spacing of the fractions in the test sample when they are eluted from a chromatographic column, thereby permitting identification of the organosulfur compounds by the interval between the times at which they are eluted and quantification of the respective organosulfur compounds by the relative intensity of their luminescence.

When the test sample is liquid the sample may be vaporized and the resulting gas passed into a chromatographic column and processed as has been described.

In other words, in the process of the present invention, the starting sample can be in the form of a gas or a liquid, as may be the case. When the sample is in the form of a gas, and when the sample contains only one organosulfur compound to be detected, the sample can be admitted directly into the reaction vessel. When the gas sample contains two or more organosulfur compounds, the sample most advantageously is passed into a gas chromatographic column where the components are retained selectively by the separatant in the column and are eluted from the separatant by a stream of carrier gas. The stream is then delivered to the reaction vessel, and the interval between the moments of elution of the respective fractions are shown on a recording chart, from which the identities of the samples can be ascertained by known methods.

When the test sample is a liquid, if only one organosulfur compound is present, and if the carrier component is volatile at the working temperature of the reaction vessel, the sample can be introduced directly into the vessel. The organosulfur compound will be reacted either in the form of a gas or in the form of a colloidal aerosol. When the test solution contains more than one organosulfur compound, the solution can be passed through a chromatographic column and the fractions eluted from the separatant can be processed as described above. The particular manner in which a sample is introduced into or prepared for introduction into the vessel is not a principal feature of the invention.

The reaction between the organosulfur compound and fluorine most advantageously is performed at very low pressure, preferably below 10 torr and, so far as results to date have shown, preferably in the range of 1 torr to 1/10 torr, as this low pressure provides superior sensitivity. Substantially no luminescence is observed when the process of the present invention is operated at normal (atmospheric) pressure.

The chromatographic column, its packing, the vaporizer, the vacuum pump and associated valves and tubes can be of the type and quality normal to the chromatographic art.

For consistency of results it is desirable to maintain the reaction at a constant temperature, and temperatures in the range of 25°–200° C. are suitable. While the reaction itself is exothermic, the amount of material which reacts and therefore the amount of heat which is evolved in each instance are small, and it is therefore desirable to provide supplementary heat to the reaction vessel as may be required for that purpose.

Preferably, the reaction vessel is a special detector cell specifically designed for this purpose. The detector cell itself may be of stainless steel sufficiently thick to withstand the low pressure within, and preferably is polished to a high reflectance on its interior to reflect as much as possible of the chemiluminescence to the photomultiplier tube. To this end the bottom of the cell may be concave. If preferred, the cell can be constructed of glass, quartz, teflon, aluminum or any teflon-coated material of adequate strength.

It is advantageous for the ports or apertures in the wall of the detector cell to be at a level between $\frac{1}{3}$ and $\frac{2}{3}$ of the height of the wall. The ports for admission of the test sample and the fluorine are advantageously located half way up the side of the detector, and the ports for admission of the tube leading to the manometer (when present) and the tube to the exhaust port are advantageously below or above that level so as to affect as slightly as possible the flow of gas in the reaction zone.

In operation, since the fluorine is added in excess, the detector cell normally has a uniformly distributed content of fluorine, and therefore chemiluminescence develops more or less throughout the cell when the test gas and the fluorine are admitted concurrently at different levels. Preferably the gas admission tubes are diametrically opposed to each other with their exit orifices a short distance (e.g. $\frac{1}{4}''$ to $\frac{3}{4}''$) apart, since with this arrangement the zone in which the gases react is small, the light from the luminescence is correspondingly more intense, and the reaction time is briefer than would otherwise be the case, with development of more intense peaks when the intensity of the emitted light is recorded on a strip chart.

It is necessary for the tubing to be in vacuum-tight engagement with the sides of the ports which they penetrate, and to that end the necessary seal may be provided by outwardly projecting sleeves or nipples which can be affixed by welding or, when highly elevated temperatures are not expected, by soldering or even by epoxy cements. Metal or synthetic plastic tubing can be affixed to the sleeves by any of the means known in the art. However, it is most convenient to employ a conventional threaded coupling for the purpose. Couplings of this type generally require that an exteriorly threaded stainless steel sleeve reamed at its outer end to provide a bevel be welded around each aperture so that the sleeves point outwardly. The vacuum-tight seal is provided by an O-ring, a travelling ferrule and an interiorly threaded undercut nut on the tube, the O-ring being of such dimensions that it can slip inside the bevel, the ferrule being of such size that it can push the O-ring into the bevel and the undercut nut having a circular flange adjacent to the tube whereby the ferrule can be pushed into engagement with the O-ring when the nut and the sleeve are mated together.

The spectral response of the preferred photomultiplier tube ranges from about 200 to 900 nm. Wavelength calibration is performed by recording the spectra of a hydrogen discharge lamp and a helium discharge lamp. Using the sharpest peaks to fit published wavelengths, the channel number to wavelength relationship is determined with a linear least squares fit.

By use of this apparatus a clean, sharp record of the chemiluminescence of the organosulfur compounds is obtained as these compounds flow from the chromatographic column, even though emission of the chemiluminescence in each instance lasts for only a few seconds.

The invention is further illustrated by the drawings, wherein.

Figure 4:
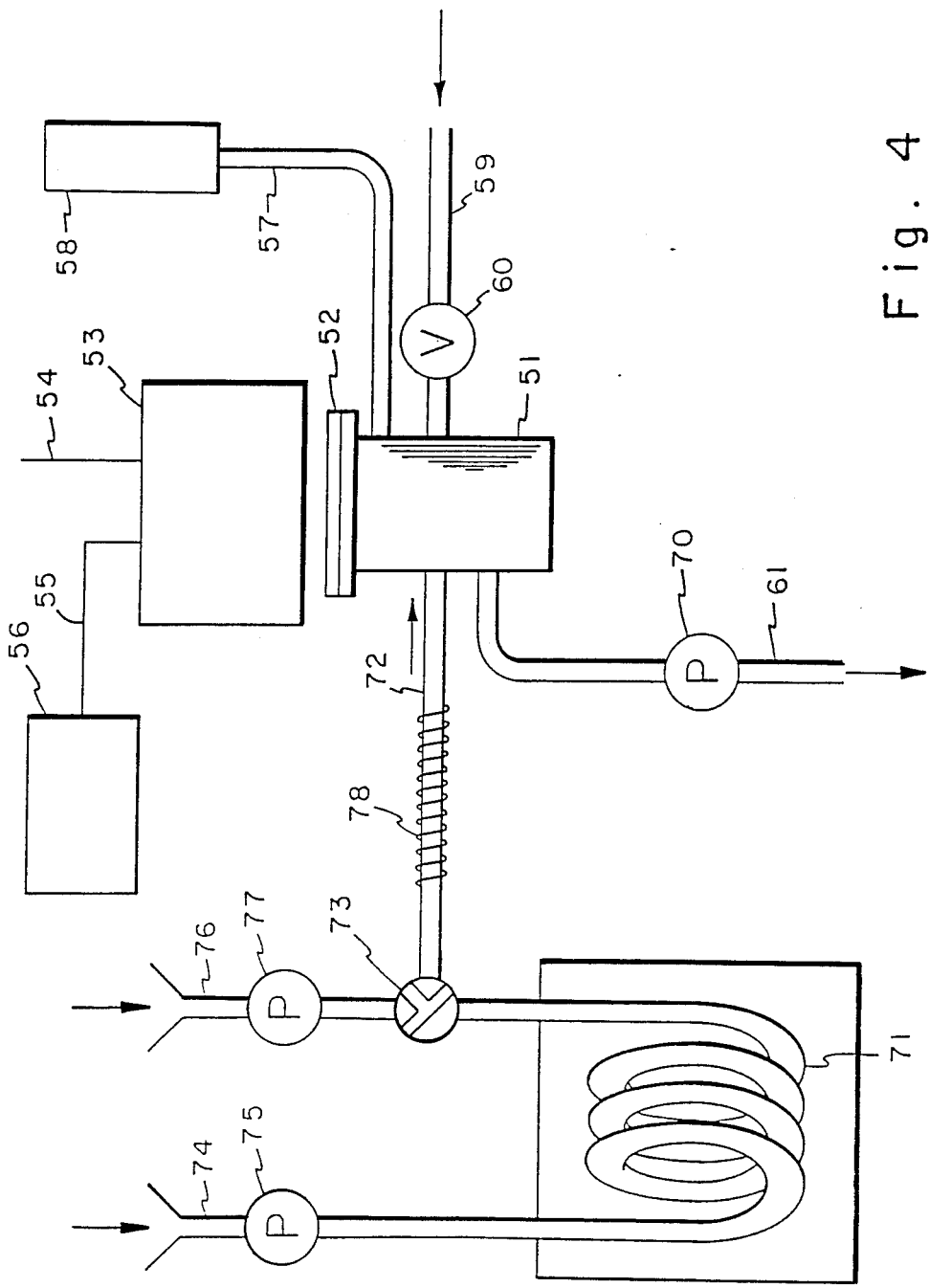
Figure 5:
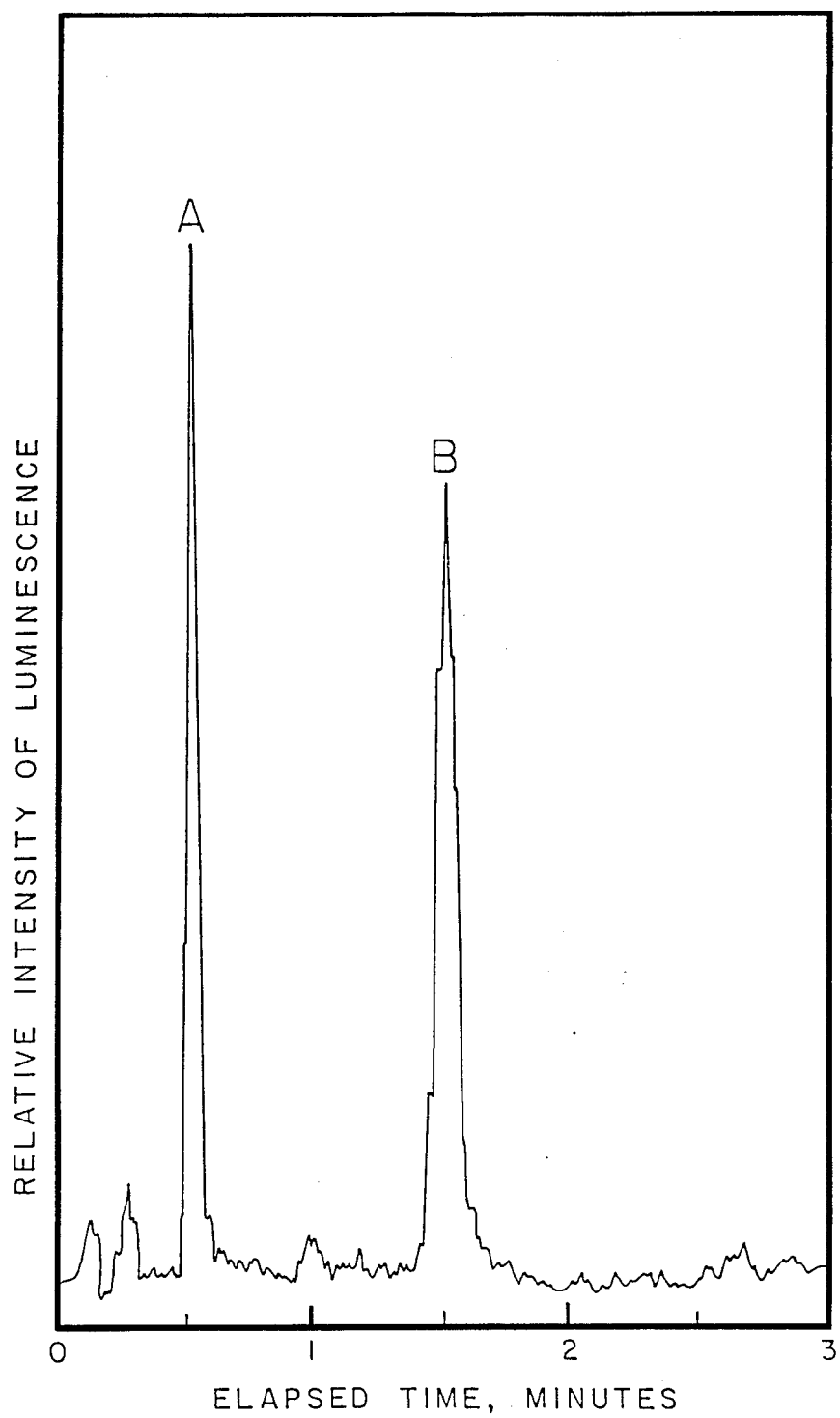

FIG. 4 is a schematic view of a detector system according to the invention showing the principal components of the system; and FIG. 5 is a graph showing as a function of time the changes in the intensity of the chemiluminescence which is developed when a sample of natural gas containing two warning gas components each in a trace amount is passed through a chromatographic column and the fractions from the column are passed successively into a detector cell against a stream of fluorine and a carrier gas with formation of highly excited hydrogen fluoride and decay of this hydrogen fluoride with emission of luminescence, as described in Example 4.

In the drawings, like numbers designate like components.

Figure 1:
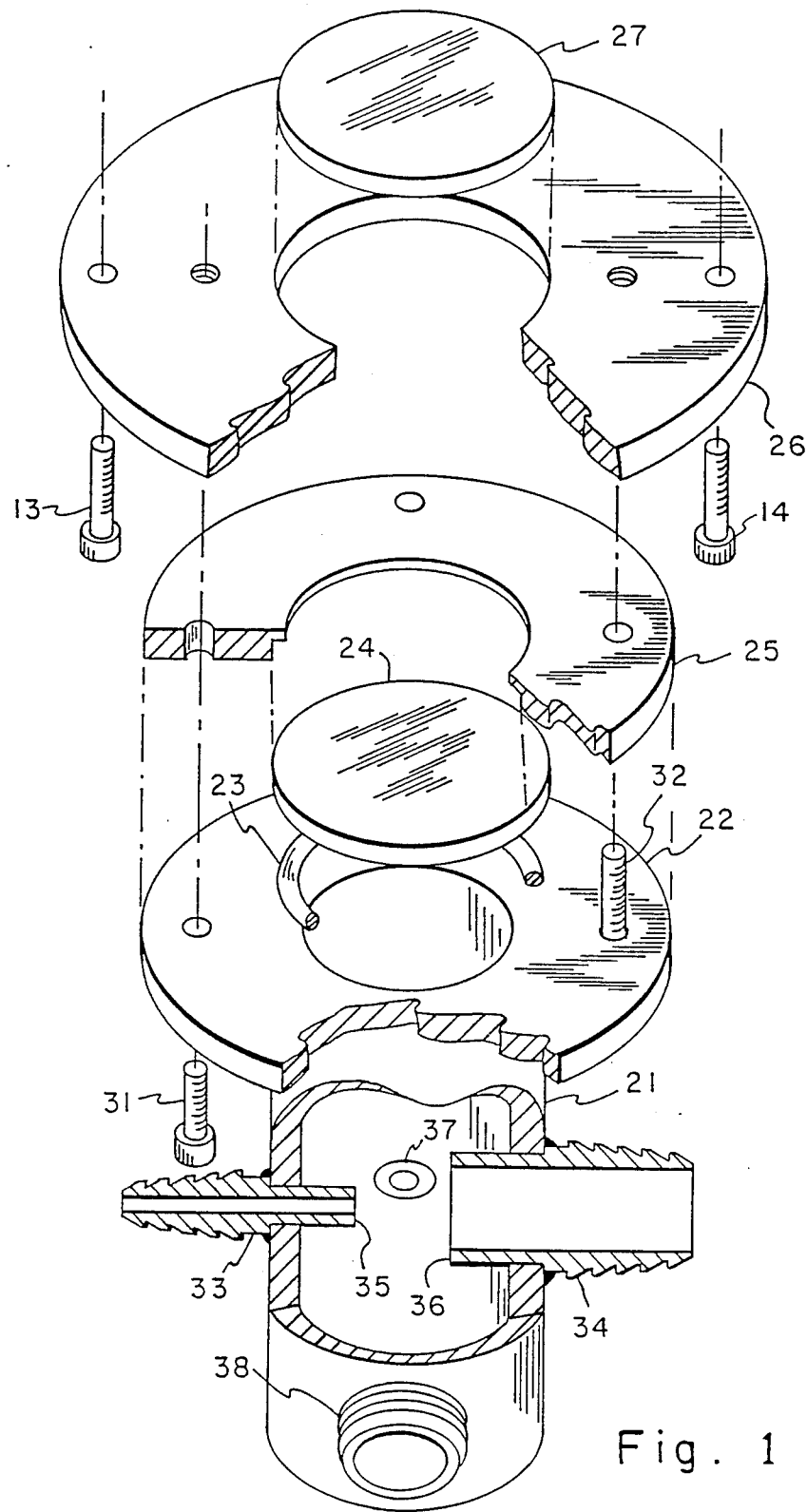
FIG. 1 is an exploded perspective view of a detector cell without associated components according to the invention, showing the principal parts of the cell.

In FIG. 1, cylindrical detector cell 21 having annular flanged top 22 is overlain successively by vacuum seal washer 23, disc-shaped viewing window 24, undercut clamping ring 25, and supporting ring 26 having an inside diameter greater than the inside diameter of clamping ring 25 thereby providing a supporting ledge for disc-shaped optional light filter 27. Bolts 13, 14, 31 and 32 are provided for clamping washer 23, window 24 and clamping ring 25 down against flange top 22 thereby providing cell 21 with a vacuum-tight transparent top. Outwardly projecting small sleeve 33 adapted to deliver liquid or gaseous test sample into cell 21 and outwardly projecting larger sleeve 34 adapted to deliver fluorine gas into cell 21 are affixed to diametrically opposite ports or apertures in cell 21 at about the mid-level thereof. A third aperture 37 is provided at a low level of the wall of cell 21, 90° from a line passing through sleeves 33 and 34, to which is affixed an outwardly projecting large sleeve (not shown) adapted to be connected to a vacuum pump for withdrawal of gaseous material from the interior of cell 21 and for production of the requisite low pressure within the cell.

Cell 1 and associated components are of gas-impermeable material strong enough to resist the pull of high vacuum, and sleeve 34 is of material which resists attack by fluorine.

Figure 2:
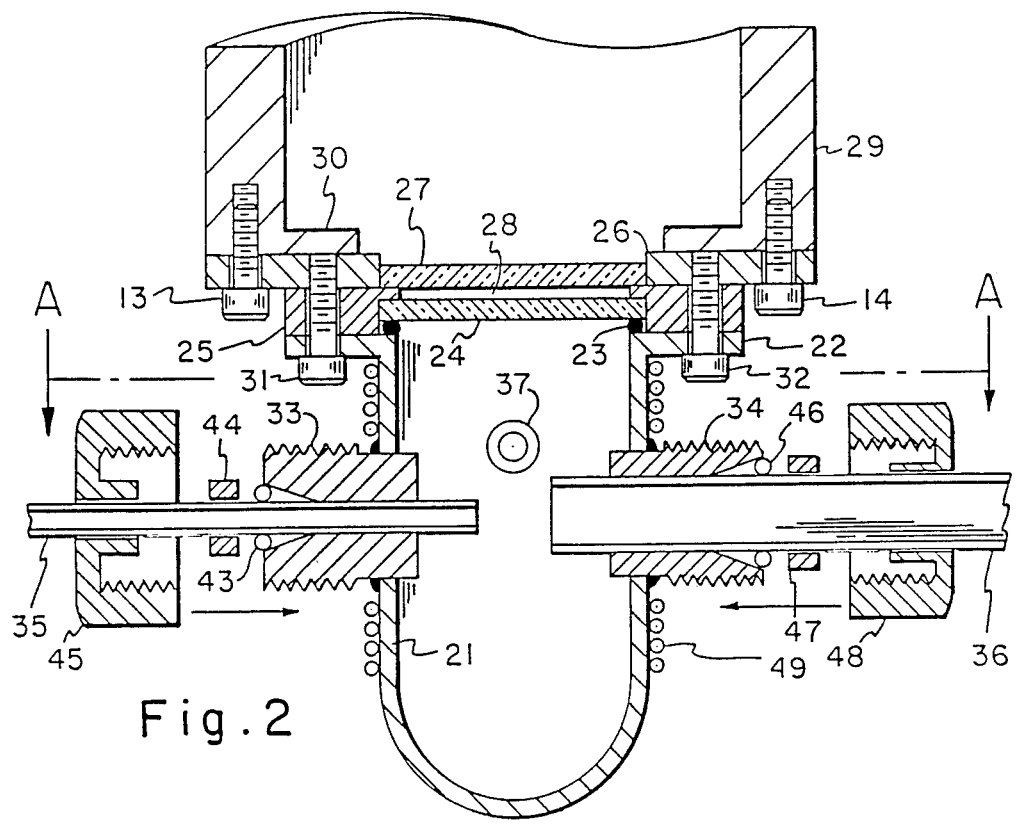
FIG. 2 is a vertical section of a preferred detector cell according to the invention with certain associated components shown, some in place and others ready for assembly.
Figure 3:
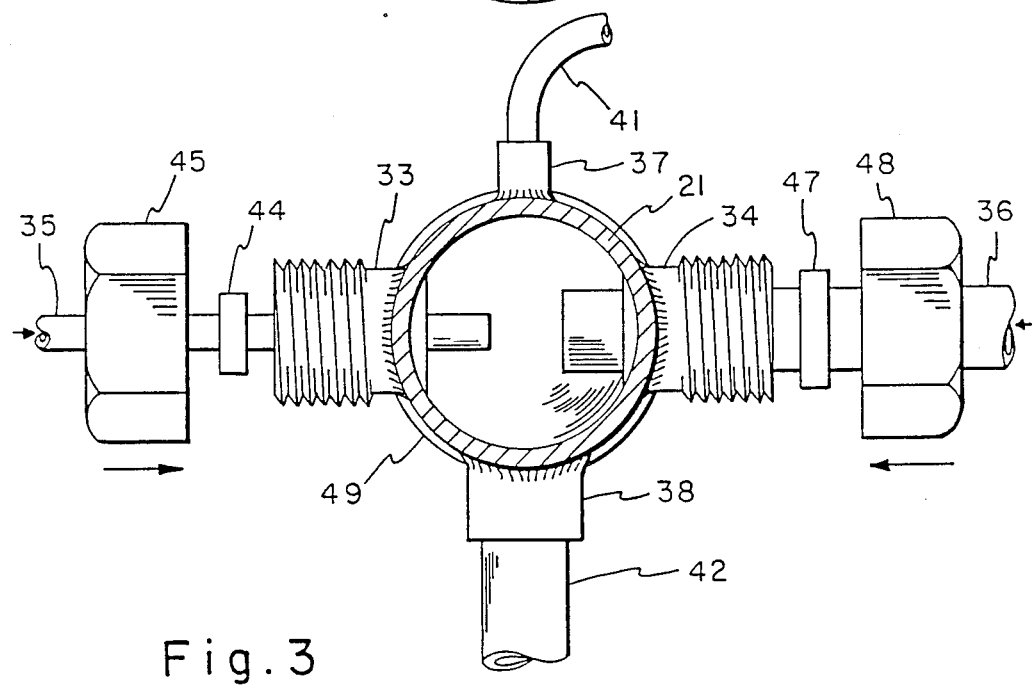
FIG. 3 is a horizontal section of the detector cell of FIG. 1 looking downwardly along lines A—A' thereof.

In FIGS. 2 and 3, optionally interiorly polished cylindrical detector cell 21 optionally having a hemispherical light focusing bottom is provided with annular flange 22 about its top, and carries annular vacuum O-seal washer 23 and quartz disc-shaped window 24 thereover. Window 24 is held in place by undercut clamping ring 25. Supporting ring 26 is centered over window 24 and has a wider inside diameter than clamping ring 25, thereby providing a circular inside ledge on which disc-shaped optical light filter 27 rests and thereby also provides air space 28 below filter 27. Cylindrical socket 29 is adapted to hold a photomultiplier tube (not shown) on inner circular ledge 30. Socket 29 is centered over light filter 27 and window 24, and rests on supporting ring 26. Bolts 31 and 32 hold rings 22 and 26 together and compress clamping ring 25 against window 24 causing O-ring washer 23 to make a vacuum-tight seal with window 24 and flange 22. Cylindrical metal sleeves 33 and 34 are welded to the outer wall of cell 21 diametrically opposite each other, and respectively support and align test sample supply tube 35 and fluorine supply tube 36 which pass through circular apertures into cell 21. Sleeves 37 and 38 are similarly welded to cell 21 and support tube 41 leading to the probe end of a capacitance manometer (not shown) and spent gas tube 42 leading to an exhaust vacuum pump (not shown). Tubes 35 and 36 each extend diametrically an equal distance into cell 21 and the ends of these tubes are spaced a short distance apart to permit the test sample and the fluorine to react together as completely and as rapidly as possible in a central portion of the cell. The ends of tubes 41 and 42 are flush with the inside wall of the cell. The cross-section interior of tubes 38 and 42 are similar.

All tubing connections are made with vacuum-tight fittings. For this purpose sleeves 33, 34, 37 and 38 are outside threaded, the exposed ends of the sleeves are undercut or reamed to produce a bevel, and the respectively associated tubes 35, 36, 41 and 42 each carry an O-ring washer adapted to slip into its adjacent bevel, a travelling ferrule adapted to push the O-ring into the bevel, and a chamfered inside-threaded nut the threads of which are adapted to mate with the threads of the adjacent sleeve. The nut is circumferentially undercut or chamfered to provide a circumferential shoe adapted to push the ferrule towards the sleeve and thereby to push the O-ring into the bevel as shown by the arrows thereby forming a vacuum-tight seal when the nut is screwed on to the sleeve. The O-ring, travelling ferrule and nut associated with sleeve 33 are respectively designated 43, 44, and 45, and these components associated with sleeve 34 are respectively designated 46, 47, and 48. Cell 21 is preferably wrapped with electrical heating tape 49 supplied with current from a variable transformer (not shown).

In FIG. 4, detector cell 51 with cap 52 containing window and light filter as shown in FIG. 1 is surmounted by photomultiplier tube 53 supplied with power by electric lines 54. The output from tube 53 is transmitted by electric lines 55 to recorder 56, which plots the intensity of chemiluminescence developed within cell 51 as a function of time. Tube 57 connects optional capacitance manometer 58 with the interior of cell 51, permitting the degree of vacuum in cell 51 to be monitored. Tube 59 containing flow control valve 60 supplies fluorine (with or without carrier gas) from a supply source (not shown) to the inside of cell 51. Tube 61 containing vacuum pump 70 is adapted to exhaust spent gas from cell 51 and to maintain a low pressure therein. Test sample is supplied from coiled chromatography column 71 to detector cell 51 by tube 72 containing three-way valve 73, which permits the test sample to be supplied to cell 51 from column 71 through feed tube 74 and high pressure pump 75 or directly into cell 51 through direct feed tube 76 and pump 77, as amy be desired. Test sample supply tube 72 is wound with optional electrical heating tape 78 supplied with current from a variable transformer (not shown) permitting liquid test sample to be vaporized before delivery to cell 51.

FIG. 5 shows the results obtained when a sample of commercial natural gas containing trace amounts of two warning component gases is analyzed by the method of Example 4 in apparatus according to FIG. 3.

The invention is further illustrated by the examples which follow. These examples are best embodiments of the invention and are not to be construed in limitation thereof. Parts are by weight unless otherwise stated.

EXAMPLE 1

The following illustrates the variety of organosulfur compounds which contain a hydrogen atom which reacts with $F_2$ to produce highly vibrationally excited hydrogen fluoride, and further illustrates the selectivity of the method.

The apparatus used corresponds with that shown in FIGS. 1–3. The gas chromatography column was a coil 6' long×3 mm in inside diameter; the interiors of the column and associated tubing and valves were washed with a 10% solution of dimethyldichlorosilane in toluene to render the surfaces non-adsorptive and inert. The column packing was of the partition type (methylsilicone fluid on inert particles, obtained from Supelco Co. as 3% SP-2100 on 100/120 Supelcoport).

The detector cell was a 4.5-cm length of 3.8 cm i.d. stainless steel tube having a welded stainless steel bottom and a flange 1" wide welded around its top. The viewing window over the top of the cell was a quartz disc 50.8 mm in diameter and 9.5 mm thick. The optical light filter which lies over the window was of the narrow band type, substantially opaque to light having a wavelength shorter than 705 nm and longer than 715 nm; the filter was adequately (55%) transparent to light having a wavelength of 706.5 nm.

The side of the cell had four holes 90° apart. Two holes opposite each other were at about mid-level of their respective sides. One of the remaining holes was somewhat higher and the other was somewhat lower so as to be apart from the intense reaction zone.

A short length of exteriorly threaded stainless steel tubing having one end reamed to produce an interior bevel was welded to each of the holes to act as a seal and support for smaller bore tubing.

The two mid-level holes were respectively for admission of the gas sample to be analyzed and for admission of the fluorine. The hole for admission of the fluorine gas-diluent composition was $\frac{1}{8}$" in diameter, and the sleeve was of the same dimension in inside diameter. The supply tube was of $\frac{3}{8}$" o.d. Pyrex glass, and a vacuum-tight seal was made between the sleeve and the tube by use of an O-ring, a travelling ferrule and an undercut pusher nut, as is shown in FIG. 1. Flow of the gas was controlled by a needle valve; the quantity of fluorine in the cell was measured by an increase in the total pressure in the cell.

A similar entrance was provided for the composition to be analyzed.

The ends of the tubes for admission of the fluorine gas composition and for admission of the composition to be analyzed were diametrically opposite in about the center of the reactor, and were about $\frac{1}{2}$" apart.

The chemiluminescence in the reactor cell was detected by a photomultiplier tube of the thermoelectrically cooled red sensitive type. It was maintained at a working temperature of $-25°$ C. The output from the tube was passed as desired either to a picoammeter or to a pulse amplifier and discriminator with photon counting by a timer/counter (Hewlett-Packard Co. No. 5308A) and converted to analog domain by a digital-to-analog converter (Hewlett-Packard Co. No. 5311B). The resulting signals were recorded on a single chart with travelling pen.

In operation, the flow of carrier gas into the chromatograph column was set at 30 ml/min and the transfer tube from the column to the detector cell was maintained at about 200° C. by electrical heating tape wound about the tube. A 95:5 helium:$F_2$ (v/v) mixture was supplied as reaction gas to the cell at room temperature at a flow rate of 300 ml/min, (without the detector cell or transfer line in place), and the exhaust vacuum pump was set to provide a vacuum of about 0.1 torr in the cell. The transfer tube was of teflon-lined stainless steel, $\frac{1}{8}$" in outside diameter. The detector cell was maintained at a working temperature in the range of 25°–200° C. by electrical heating tape. In each instance the test samples were a 1 ppm solution of the analyte in hexane.

Strong luminescence was recorded for each of the following analytes except thiophene, which returned a useful but reduced fluorescence:

Mercaptans

Ethanethiol
2-Mercaptoethanol
1,2-Ethanedithiol
1,3-Propanedithiol
1-Butanethiol
Ethyl mercaptoacetate
t-Butylmercaptan
1-Hexanethiol
Benzenethiol
o-Aminobenzenethiol
1-Heptanethiol 1-Octanethiol
1-Dodecanethiol

Sulfides

Methyl sulfide
Ethyl sulfide
Allyl sulfide
n-Butyl sulfide
iso-Butyl sulfide
t-Butyl sulfide
iso-Amyl sulfide
Phenyl sulfide
n-Heptyl sulfide
Thiophene
iso-Amyl disulfide
n-Butyl disulfide

Esters and Misc.

Malathion
Parathion
Dimethyl sulfoxide

The procedure was repeated with $CS_2$ (carbon disulfide), ethyl acetate, ethanol, hydrogen sulfide, methane, ethane, propane, benzene, COS (carbonyl sulfide) and $SO_2$ (sulfur dioxide), but no luminescence was detected.

EXAMPLE 2

The following illustrates the limits of detection of certain organosulfur compounds of the previous example. The limit of detection is the smallest amount of the compound in its carrier gas or liquid which provides a signal at least twice as high as the background noise on the chemiluminescence chart.

The procedure of Example 1 was repeated with the compounds shown below. In each instance the carrier solvent was hexane and the volume of the sample which was introduced into the detector cell was 1 µl. Résults were as follows:

| Compound | Detection Limit pg /µl |
| --- | --- |
| Ethyl mercaptan | 52 |
| Dimethyl sulfide | 63 |
| 1,3-Propanedithiol | 29 |
| Allyl sulfide | 19 |
| sec.-Butyl sulfide | 104 |
| 1-Octanethiol | 63 |
| n-Butyl disulfide | 63 |
| Dimethyl sulfoxide | 94 |

EXAMPLE 3

The following illustrates the application of the present invention to the detection of residual amounts of organosulfur insecticides on fruit.

A quantity of apples from an orchard which had been sprayed with Malathion,

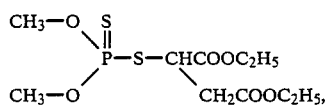

was washed with water at room temperature. A 500-cc sample of the wash water was evaporated to 10 ml under vacuum, and a 1 µl sample was introduced into the detector system of Example 1. The tracing obtained from the chemiluminescence recorder was substantially the same as that obtained with a reference sample of Malathion solution.

EXAMPLE 4

For reasons of safety it is often desirable to monitor the amount of warning component present in natural gas, which is odorless. Natural gas typically is composed of 85% methane, 9% ethane, 3% propane, 2% nitrogen and 1% butane. The content of warning gas (typically one or more organosulfur compounds) in a sample of household natural gas was determined according to the method and apparatus of Example 1, except as follows: The diameter of the absorption column was 2 mm, the column packing was of the partition type (GP 60/80 Carbopack B/1.5% XE-60/1% $H_3PO_4$), the temperature of the column was 125° C. and the flow rate of the carrier gas (helium) was 35 ml/min. The size of the sample was 1.0 µl.

Comparison of the resulting graph (FIG. 3) with laboratory reference standard graphs shows that the peaks which developed after 0.5 minute and 1.5 minute (peaks A and B) recorded chemiluminescence derived respectively form dimethyl sulfide and t-butyl mercaptan.

EXAMPLE 5

The following illustrates the quantitative determination of dimethyl sulfide in beer. Dimethyl sulfide is formed in trace amounts during the fermentation step in beer manufacture (usually in amounts in the range of 0.05 to 5 ppm), and small changes in the amount of dimethyl sulfide thus produced cause noticeable changes in the taste of the beer.

The general procedure of Example 1 was followed with the same apparatus, except as follows. The diameter of the chromatography column was 2 mm, its temperature was 45° C. and the rate of flow of the carrier gas was 35 ml/min.

To a bottle of beer was added 0.3 ppm of diethyl sulfide to provide a reference standard, and the bottle was closed to allow the vapor in the headspace to come to equilibrium with the beer. A 0.5 ml sample of the vapor was then withdrawn and introduced into the gas chromatograph column and processed as described in Example 1. The chart which registered the intensity of the luminescence detected by the photon counter showed only two peaks, one for dimethyl sulfide and the other for the diethyl sulfide. Comparison of the height of the dimethyl sulfide peak with the height of the diethyl sulfide peak permitted the concentration of dimethyl sulfide in the beer to be determined, since the relationship between the two peaks was linear. In this manner an amount of dimethyl sulfide as small as 0.088 ppm could be determined.

Further examples of processes, apparatuses, and applications within the spirit and scope of this invention will be apparent to those skilled in the art upon consideration of the foregoing description and consequently only such limitations as appear in the appended claims should be placed thereon.

We claim:

1. A process for the selective detection of an organosulfur compound having at least one fluorine-reactive hydrogen atom and at least one sulfur atom, which process comprises reacting in gaseous medium under reduced pressure an effective amount of molecular fluorine with said organosulfur compound to form vibrationally excited hydrogen fluoride therefrom, and detecting the chemiluminescence at 650–750 nm which is produced when said excited hydrogen fluoride decays to its ground state.

2. A process according to claim 1 wherein said organosulfur compound is in colloidal aerosol state.

3. A process according to claim 1 wherein said gaseous medium has a pressure between about 1/10 and 10 torr.

4. A process according to claim 1 wherein the temperature of said gaseous medium is between about 25° C. and 300° C.

5. A process according to claim 1, wherein the weight of said fluorine is between about 100 and 1,000 times the weight of said organosulfur compounds.

6. A process according to claim 1 wherein the weight of said organosulfur compound is between $10^{-3}$ and $10^{-8}$ of the weight of said gaseous medium.

7. A process according to claim 1 wherein the weight of said fluorine is between about 1/25 and 1/3 of the weight of said gaseous medium.

8. A process according to claim 1 wherein said organosulfur compound is a thiol.

9. A process according to claim 1 wherein said organosulfur compound is a sulfide.

10. A process according to claim 1 wherein said organosulfur compound is a thioester.

11. A process for the selective detection of an organosulfur compound having at least one fluorine-reactive hydrogen atom and at least one sulfur atom in admixture with at least one other compound not having this composition, which comprises passing said admixture into a chromatographic column thereby retaining components of said admixture as fractions on separatant in said column, eluting said fractions from said separatant, passing said fractions as a stream into a detector cell containing molecular fluorine thereby forming vibrationally excited hydrogen fluoride by reaction of said organosulfur compound with said molecular fluorine under reduced pressure, and detecting the chemiluminescence at 650–750 nm which is produced when said hydrogen fluoride decays to its ground state.

12. A process according to claim 11 wherein said organosulfur compound is in solution in normally liquid carrier fluid and said carrier fluid is volatilized before said admixture is passed into said chromatographic column.

13. A process according to claim 11 wherein said organosulfur compound is in solution in normally liquid carrier fluid and said carrier fluid has a vaporization temperature below the temperature of said detector cell.

14. A process according to claim 11 wherein said organosulfur compound is in solution in normally liquid carrier fluid and said admixture is volatilized after said admixture has passed from said chromatographic column.

15. A process according to claim 11 wherein said fractions are passed as a gaseous stream directly into a stream of fluorine gas.

16. A process according to claim 11 wherein at least part of said chemiluminescence passes through a color filter which transmits only light having a wavelength in the range of 650–750 nm, continuously recording the intensity of the light transmitted by said filter as a function of time, and comparing the resulting records with laboratory reference plots, whereby said organosulfur compound is detected.

17. A process according to claim 16 wherein the flux of the light transmitted by said filter is measured by the action of a photomultiplier tube.

* * * * *